(12) United States Patent
Balicki et al.

(10) Patent No.: US 10,166,080 B2
(45) Date of Patent: Jan. 1, 2019

(54) COOPERATIVELY-CONTROLLED SURGICAL ROBOTIC SYSTEM WITH REDUNDANT FORCE SENSING

(71) Applicant: THE JOHNS HOPKINS UNIVERSITY, Baltimore, MD (US)

(72) Inventors: Marcin Arkadiusz Balicki, Baltimore, MD (US); Kevin C. Olds, Baltimore, MD (US); Russell H. Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 146 days.

(21) Appl. No.: 15/179,438

(22) Filed: Jun. 10, 2016

(65) Prior Publication Data

US 2016/0361125 A1 Dec. 15, 2016

Related U.S. Application Data

(60) Provisional application No. 62/175,080, filed on Jun. 12, 2015.

(51) Int. Cl.
*B25J 19/06* (2006.01)
*A61B 34/30* (2016.01)
*B25J 9/16* (2006.01)
*B25J 13/08* (2006.01)
*A61B 17/00* (2006.01)

(52) U.S. Cl.
CPC ............. *A61B 34/30* (2016.02); *B25J 9/1676* (2013.01); *B25J 13/085* (2013.01); *B25J 19/06* (2013.01); *A61B 2017/0003* (2013.01)

(58) Field of Classification Search
None
See application file for complete search history.

(56) References Cited

U.S. PATENT DOCUMENTS

| 5,397,323 A | 3/1995 | Taylor et al. |
| 5,417,210 A | 5/1995 | Funda et al. |

(Continued)

OTHER PUBLICATIONS

De Luca et al., "Collision Detection and Safe Reaction with the DLR-III Lightweight Manipulator Arm," Proceedings of the IEEE/RSJ International Conference on Intelligent Robots and Systems, Beijing, China, pp. 1623-1630 (Oct. 2006).

(Continued)

*Primary Examiner* — Truc M Do
(74) *Attorney, Agent, or Firm* — Venable LLP; Henry J. Daley; Laura G. Remus (57) ABSTRACT

A cooperatively controlled robotic system includes a main robot assembly, and an arm assembly comprising a proximal end and a distal end. The arm assembly is connected to the main robot assembly at the proximal end. The system also includes a tool assembly connected to the arm assembly at the distal end, a first force sensor between the distal end of the arm assembly and the tool assembly, and a second force sensor between the proximal end of the arm assembly and the main robot assembly. The system includes a control system that is configured to determine a force applied at the first force sensor based on a force detected by the second force sensor, and to compare the determined force to a force detected by the first force sensor to detect a failure of at least one of the first and second force sensors.

16 Claims, 5 Drawing Sheets

(56) References Cited

U.S. PATENT DOCUMENTS

| | | | |
|---|---|---|---|
| 5,572,999 | A | 11/1996 | Funda et al. |
| 5,749,362 | A | 5/1998 | Funda et al. |
| 5,887,121 | A | 3/1999 | Funda et al. |
| 6,201,984 | B1 | 3/2001 | Funda et al. |
| 7,035,716 | B2 | 4/2006 | Harris et al. |
| 8,398,541 | B2 | 3/2013 | DiMaio et al. |
| 8,911,429 | B2 * | 12/2014 | Olds ............... B25J 9/0051 340/12.22 |
| 9,815,206 | B2 | 11/2017 | Balicki et al. |
| 2004/0111183 | A1 * | 6/2004 | Sutherland ............ A61B 34/75 700/245 |
| 2007/0021738 | A1 * | 1/2007 | Hasser ............... A61B 8/12 606/1 |
| 2009/0036902 | A1 * | 2/2009 | DiMaio ............... A61B 8/12 606/130 |
| 2009/0299142 | A1 * | 12/2009 | Uchiyama ......... A61B 1/00158 600/118 |
| 2010/0094312 | A1 * | 4/2010 | Ruiz Morales ........ B25J 13/085 606/130 |
| 2011/0106102 | A1 * | 5/2011 | Balicki .............. A61L 33/1005 606/130 |
| 2012/0071890 | A1 * | 3/2012 | Taylor ................. A61B 5/6817 606/129 |
| 2012/0172893 | A1 * | 7/2012 | Taylor ............... A61B 1/00172 606/130 |
| 2012/0226150 | A1 * | 9/2012 | Balicki ............... A61B 5/0066 600/424 |
| 2013/0131867 | A1 * | 5/2013 | Olds ................... B25J 9/0051 700/260 |
| 2013/0190734 | A1 * | 7/2013 | Taylor ................. A61F 9/007 606/1 |
| 2013/0304258 | A1 * | 11/2013 | Taylor ................ A61B 19/2203 700/260 |
| 2014/0094968 | A1 * | 4/2014 | Taylor ................... B25J 13/006 700/257 |

OTHER PUBLICATIONS

Eldridge, et al., "A Remote Center of Motion Robotic Arm for Computer Assisted Surgery", Robotica, vol. 14-1 (Jan.-Feb.), pp. 103-109, 1996 (Abstract only).

Funda et al., "Comparison of two mainpulator designs for laparoscopic surgery", in 1994 SPIE Int's Symposium on Optical Tools for Manufacturing and Advanced Automation, Boston (1994).

Funda et al., "Constrained Cartesian motion control for teleoperated surgical robots", IEEE Transactions on Robotics and Automation, vol. 12-3, pp. 453-466 (1996).

Funda et al., "Control and evaluation of a 7-axis surgical robot for laparoscopy", in Proc 1995 IEEE Int. Conf. on Robotics and Automation, Nagoya, Japan (May 1995).

Funda et al., "Optimal Motion Control for Teleoperated Surgical Robots", in 1993 SPIE Intl. Symp. on Optical Tools for Manuf. & adv. Autom., Boston (1993).

He et al., "A Multi-Function Force Sensing Instrument for Variable Admittance Robot Control in Retinal Microsurgery," IEEE Int Conf Robot Autom, pp. 1-28 (2014).

Singh et al., "Physiological Tremor Amplitude during Retinal Microsurgery," IEEE, pp. 171-172 (2002).

Taylor et al., "A Telerobotic Assistant for Laparoscopic Surgery," IEEE Eng Med Biol, vol. 14, No. 3, pp. 279-288 (1995).

De Luca et al., "Sensorless robot collision detection and hybrid force/motion control." Proceedings of the 2005 IEEE International Conference on Robotics and Automation, pp. 999-1004 (2005).

* cited by examiner

COOPERATIVELY-CONTROLLED SURGICAL ROBOTIC SYSTEM WITH REDUNDANT FORCE SENSING

This application claims priority to U.S. Provisional Application No. 62/175,080 filed Jun. 12, 2015, the entire content of which is hereby incorporated by reference.

This invention was made with Government support under grant EEC-9731478, awarded by the National Science Foundation Engineering Research Center for Computer-Integrated Surgical Systems and Technology. The Government has certain rights in the invention.

BACKGROUND

1. Technical Field

The field of the currently claimed embodiments of this invention relates to surgical robots, and more particularly to cooperatively-controlled surgical robotic systems with redundant force sensing.

2. Discussion of Related Art

The SteadyHand micromanipulation robot, disclosed in U.S. Pat. No. 8,911,429, which is hereby incorporated by reference, is a force-controlled surgical device with a primary force/torque sensor located between the last joint of the robot and the surgical instrument adapter. When the surgeon applies a force on the handle of the instrument attached to the adapter, the forces and torques measured by the force/torque sensor are resolved at the handle and the robot complies with the forces and torques by moving the instrument in a corresponding direction. The reliability of the primary force/torque sensor is critical to meeting the stringent safety and efficiency requirements common in surgical applications.

Force/torque sensors are susceptible to many modes of failure due to accidents, misuse, or hazards in the environment. They can provide incorrect measurements from temperature changes, electrical noise, or permanent mechanical deformations. The SteadyHand robot uses a force/torque sensor as the main human interaction input for controlling the motion of the robot. In the case where the measurements are incorrect, it is possible that the robot will react in an unexpected and possibly unsafe manner. This is especially undesirable in high-risk scenarios such as surgery where any undesirable motion of the surgical instrument held by the robot could cause severe injury and even death of the patient. In addition, a robot operating in vicinity of humans should be able to detect the intentions of the operator, detect collisions between itself and objects in its workspace, and have intuitive robot interaction methods. Accordingly, improved systems and methods are needed for ensuring accurate force sensing in cooperatively-controlled surgical robots.

SUMMARY

According to some embodiments of the invention, a cooperatively controlled robotic system includes a main robot assembly, and an arm assembly comprising a proximal end and a distal end. The arm assembly is connected to the main robot assembly at the proximal end. The cooperatively controlled robotic system also includes a tool assembly connected to the arm assembly at the distal end, a first force sensor between the distal end of the arm assembly and the tool assembly, and a second force sensor between the proximal end of the arm assembly and the main robot assembly. The cooperatively controlled robotic system includes a control system in communication with the main robot assembly, the arm assembly, the tool assembly, the first force sensor, and the second force sensor. The control system is configured to determine a force applied at the first force sensor based on a force detected by the second force sensor. The control system is further configured to compare the determined force to a force detected by the first force sensor. The control system is further configured to detect a failure of at least one of the first and second force sensors based on the comparison.

According to some embodiments of the invention, a method for redundant force sensing in a cooperatively controlled robotic system includes measuring, from a first position, at least one force component applied by a user to a tool assembly, and measuring, from a second position, the at least one force component applied by the user to the tool assembly. The method further includes determining a force applied at the first position based on the measurement from the second position, comparing the determined force to the measurement from the first position, and detecting at least one of a sensor failure, an arm assembly collision, and a user-robot interaction based on the comparison.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the invention are directed to cooperatively controlled robot control, and specifically to force/torque sensing to improve robustness and safety of cooperatively controlled robotic systems. Ergonomics and intuitive operation of the cooperatively controlled robotic system platform are also addressed. Some embodiments of the invention are directed to force/torque failure detection, robot arm collision detection, and detection of user-robot interactions.

Figure 1:
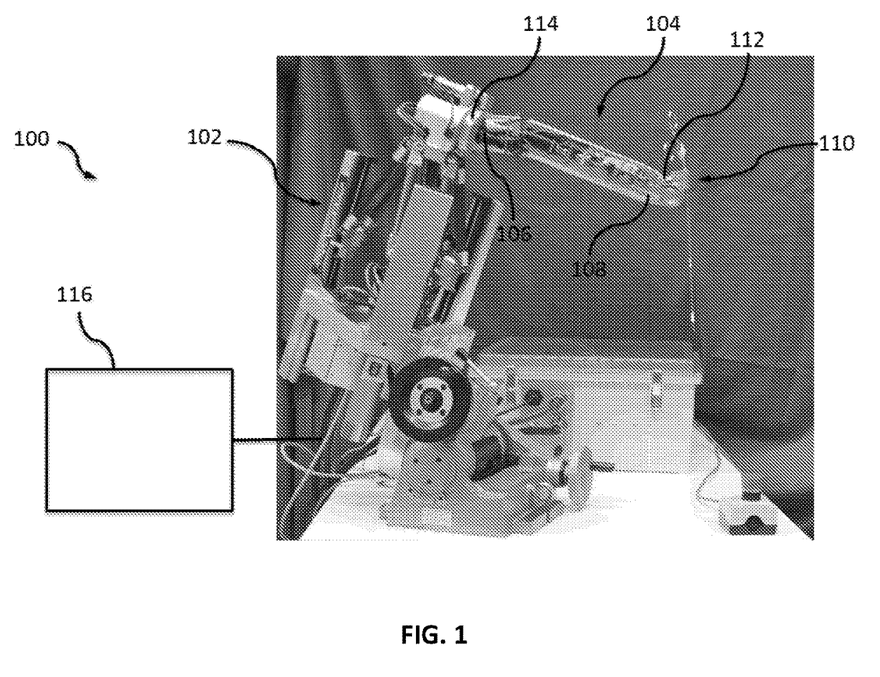
FIG. 1 shows a cooperatively controlled robot according to some embodiments of the invention.

A cooperatively controlled robot according to some embodiments of the invention is shown in FIG. 1. The cooperatively controlled robot 100 includes a main robot assembly 102 comprising mechanical links connected by actuated joints, and an arm assembly 104 comprising a proximal end 106 and a distal end 108. The arm assembly 104 is connected to the main robot assembly 102 at the proximal end 106. The cooperatively controlled robot 100 includes a tool assembly 110 connected to the arm assembly 104 at the distal end 108. The cooperatively controlled robot 100 includes a first force sensor 112 between the distal end 108 of the arm assembly 104 and the tool assembly 110, and a second force sensor 114 between the proximal end 106 of the arm assembly 104 and the main robot assembly 102. The cooperatively controlled robot 100 includes a control system 116 in communication with the main robot assembly 102, the arm assembly 104, the tool assembly 110, the first force sensor 112, and the second force sensor 114. The control system 116 is configured to determine a force applied at the first force sensor 112 based on a force detected by the second force sensor 114, to compare the determined force to a force detected by the first force sensor 112, and to detect a failure of at least one of the first force sensor 112 and the second force sensor 114 based on the comparison.

According to some embodiments of the invention, the main robot assembly provides translation using a Delta robot stage, but this can be replaced by any combination of actuated robotic architecture that includes translations and or/rotations. According to some embodiments, the arm assembly contains two rotary joints. The arm assembly can include one or more translation joints, depending on task requirements, or a combination of rotary and translation joints.

A SteadyHand Robot is an example of a cooperatively controlled robot (also known as admittance control and force control) where the surgeon and robot share the control of the surgical instrument. Examples are the JHU EyeRobot and the REMS system. In the cooperative control paradigm the operator and the robot both hold the surgical instrument. The force exerted by the operator guides the robot to comply with the operator's movement using an admittance control method. Although the work presented here is primarily directed to admittance controlled robots, most of the methods apply to impedance controlled robots as well. According to some embodiments, the motion of the robot and the surgical instrument are in the direction of the force that the surgeon applies to the surgical instrument. Using various control modes, the cooperatively controlled robot can provide precise, tremor-free, smooth, and steady manipulation. The result will be a manipulation system with the precision and sensitivity of a machine, but with the manipulative simplicity, immediacy, and the natural hand-eye coordination of hand-held instruments to which the surgeon is already accustomed.

The cooperatively controlled robot senses the forces (via a 6 DOF force/torque sensor, for example) exerted by the surgeon on the surgical instrument handle and moves the instrument to comply with the exerted forces. Through this partnership, the surgeon directly controls the instrument that is used to operate on the patient, and the surgeon's physiological hand tremor is significantly reduced. This is in contrast with tele-operated systems, wherein the surgeon controls a joystick remotely and the robot moves the instrument. The 6 DOF force/torque (FT) sensor is predominantly used in interpreting the surgeon's intentions for controlling the motion of the surgical instrument. The deflection of the actual instrument from forces from physical handling when the robot is not moving is minimal due to a very stiff structural design and non-backdrivable nature of the actuators.

Cooperatively controlled robots typically have a single FT sensor. However, the single FT sensor is prone to damage, and can give incorrect force measurements due to intermittent environmental conditions such as rapid temperature change, electrical noise, or mechanical damage. The following system and methods address this by incorporating additional force sensing capabilities on the robot itself.

Figure 2:
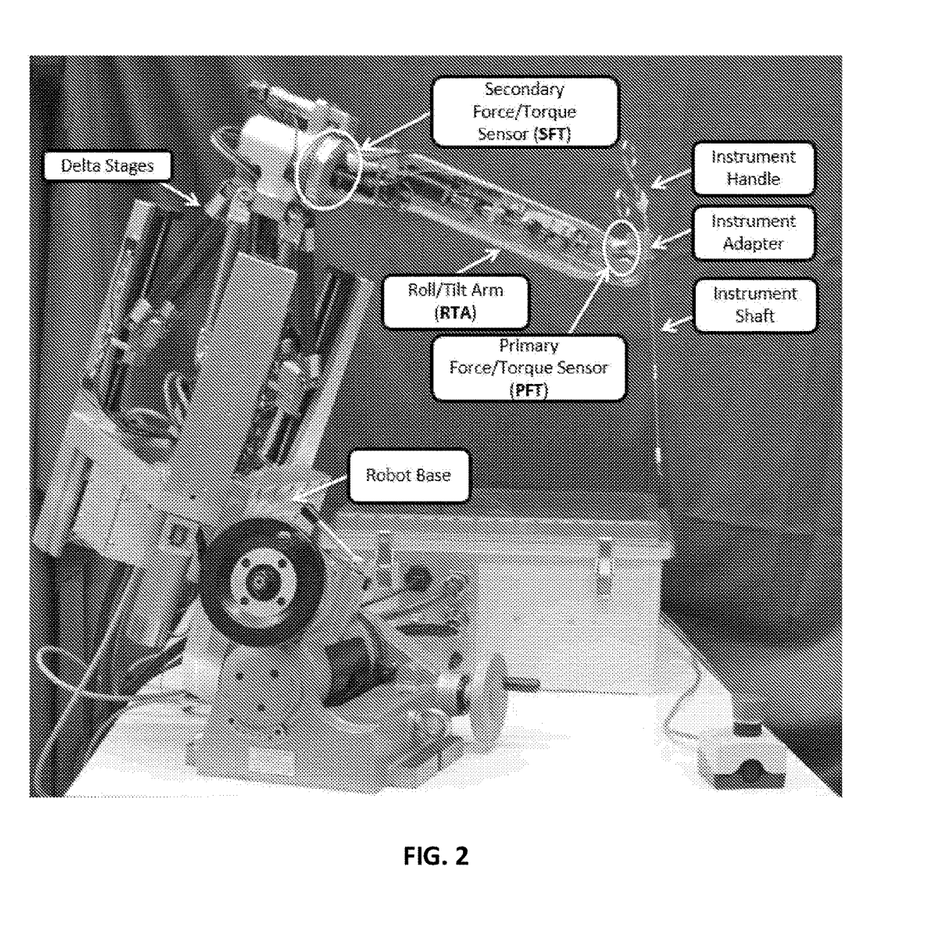
FIG. 2 shows the components of a cooperatively controlled robot with a Secondary Force/Torque sensor (SFT)

In the embodiments below, at least one additional force/torque sensor (Secondary Force/Torque Sensor (SFT)) is integrated into the robot structure between the handle force/torque sensor and the base of the robot. The redundant sensing capability provides information for additional methods that improve robot usability, reliability, and provide novel robot-user interaction functionality. Besides the standard sensor redundancy to ensure safe motion control for surgical applications, the additional force sensing can be used to provide new interaction methods that save time, reduce peripherals, and are intuitive to the operator. FIG. 2 shows the components of a cooperatively controlled robot having an SFT according to some embodiments of the invention. The methods presented here are agnostic to the implementation of the force/torque sensors, which can be stand-alone devices integrated in between the robot components, or can include sensing elements integrated into the body of the robot using its mechanical compliance for sensing.

Figure 3:
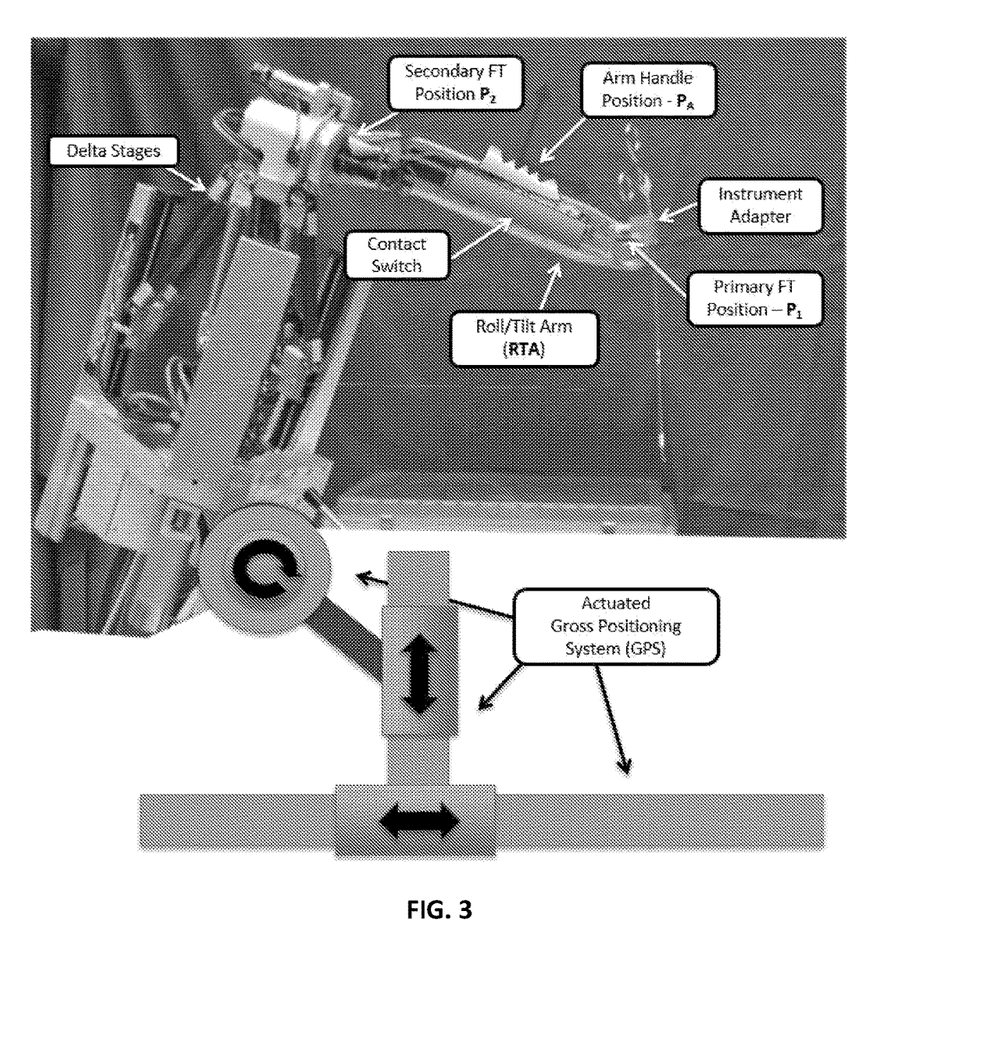
FIG. 3 illustrates a Gross Positioning System (GPS) and cooperatively controlled robot with a Roll/Tilt Arm (RTA) handle and switch.

The cooperatively controlled robotic system according to some embodiments of the invention can include a handle on the RTA, as shown in FIG. 3. A user can grasp the handle to aid in positioning the robot. The handle can include an arm contact switch (ACS) that can detect when the user grasps the handle.

According to some embodiments of the invention, the cooperatively controlled robotic system includes an actuated gross positioning system (GPS) to provide a convenient way to adjust the overall position of the cooperatively controlled robotic system in the surgical workspace. FIG. 3 illustrates an example GPS. The GPS can be driven with an external joystick, or through cooperative control, as described below. According to some embodiments, the GPS is mounted on the operating bed rail. According to some embodiments, the GPS is part of a cart that is connected to an operating table during surgery. The GPS can provide motion in a single dimension, such as lateral movement along a rail, or motion in additional dimensions. FIG. 3 illustrates a GPS that allows linear horizontal and vertical motion, as well as rotation. Other embodiments may include just one or two of these three types of motion.

Figure 4A:
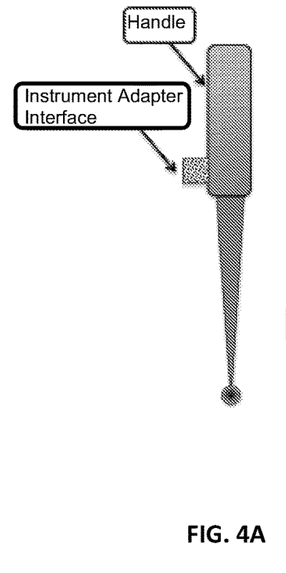
FIG. 4A shows a pointing instrument (PI) according to some embodiments.
Figure 4B:
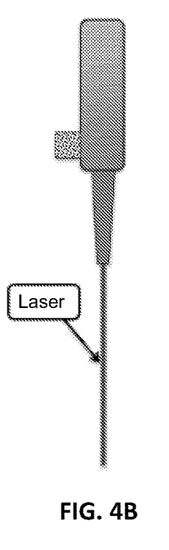
FIG. 4B shows a PI that includes a laser pointer inside the shaft.
Figures 4C, 4D:
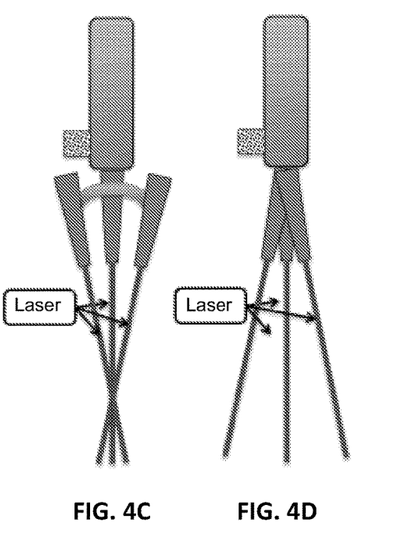
FIG. 4C shows a PI that includes multiple lasers with crossing beams.
FIG. 4D shows a PI that includes multiple lasers with diverging beams.

Cooperatively controlled robotic systems are outfitted with a method to recognize the type of instrument located in the instrument adapter. According to some embodiments of the invention, a special non-surgical positioning instrument (PI) can be designated for adjusting the GPS. FIG. 4A shows an example PI with a handle, a straight shaft pointer, and a ball-shaped end. For safety reasons the PI can be made of hard silicone to comply in case of a collision. According to some embodiments, the PI includes a laser pointer inside the shaft (aligned with the instrument axis) to provide an aiming beam. An example of such a PI is illustrated in FIG. 4B. According to some embodiments, the PI includes multiple lasers mounted on the instrument so that their beams intersect at a predefined distance from the handle or robot body. This is illustrated in FIG. 4C. When the tool is in a desired positioned, the laser beams create a projection of a predefined pattern (dot(s), circle, square, etc.,) projected on the target surface. This can eliminate the need for a long instrument shaft to indicate the reach of the robot, or ideal alignment. According to some embodiments, the lasers can be arranged in a cone to show the range of motion of the instrument, as shown in FIG. 4D. This may be especially beneficial in the case where the instrument is asymmetric and swivels about the instrument shaft.

Methods for controlling a cooperatively controlled robotic system with redundant force sensing according to some embodiments of the invention are described in detail below. The methods can be implemented by a control system, such as the cooperatively controlled robot's control system. The control system can be a dedicated "hard-wired" device, or it can be a programmable device. For example, it can be, but is not limited to, a processor, a personal computer, a work station, or any other suitable electronic device for the particular application. In some embodiments, it can be integrated into a unit or it can be attachable, remote, and/or distributed.

Handle Force/Torque Sensor Failure Detection

Figure 5:
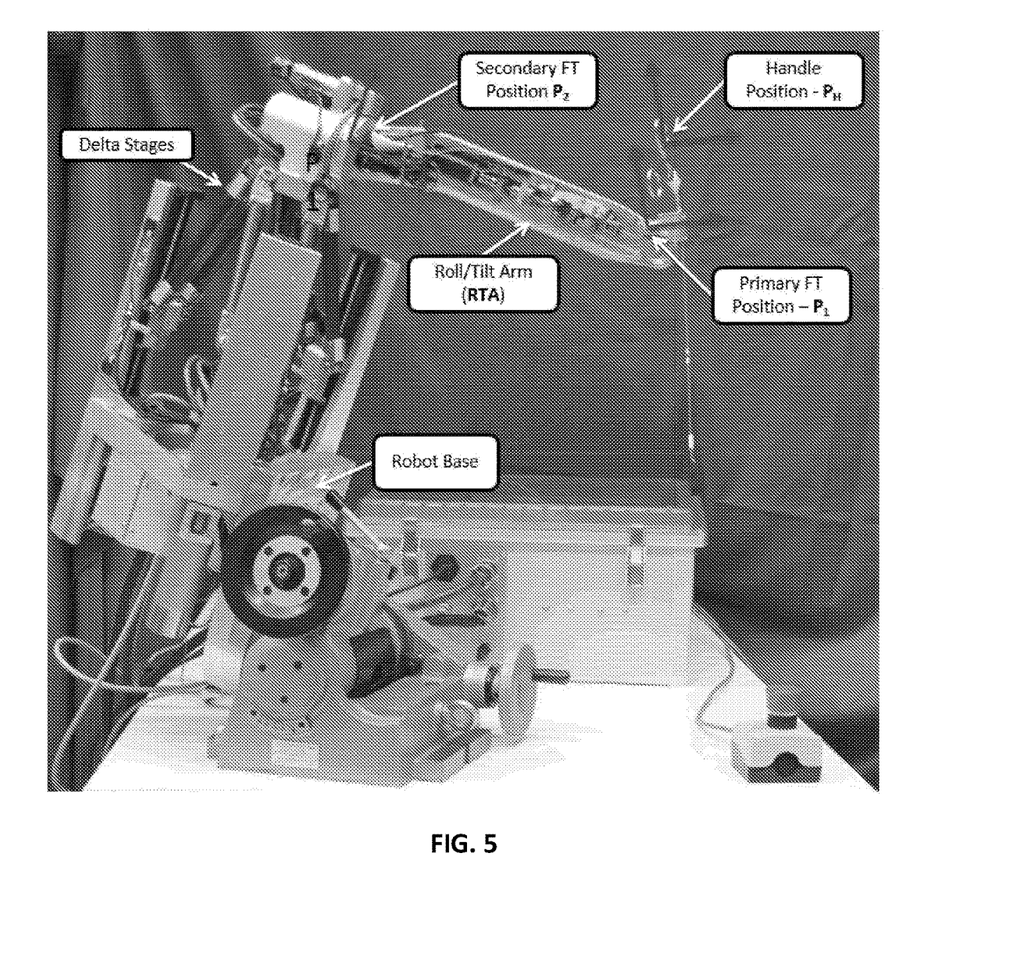
FIG. 5 illustrates positions where forces and torques are resolved according to some embodiments of the invention.

In the event of a failure in the primary force sensor (PFT), the SFT can be used to cross-check the force values to determine that a failure has occurred, and stop the motion of robot. FIG. 5 illustrates positions where forces and torques can be resolved for failure detection. The initial consistency check is done by resolving the SFT at location $P_1$ ($SFT_1$) and comparing the force/torque values to those reported by PFT also resolved at $P_1$ ($PFT_1$). Before the comparison is made the $SFT_1$ measurement is calculated to account for the weight of the Roll/Tilt Arm (RTA) between the two sensor coordinate frames, and the given robot pose. The RTA can also be referred to as an "arm assembly." However, the meaning of the term "arm assembly" is not limited to the roll-tilt arm described herein, and can be used to refer to any assembly that allows for orientation and/or translation, for example, orientation or translation of a tool assembly to which the orientation assembly may be attached.

If the magnitude of $PFT_1$ is not equal to that of $SFT_1$ (corrected for the weight of the RTA) within some tolerance (e), then one of the force/torque sensors is not functioning as expected. If the difference persists (diff>e) for a predefined amount of time (t), the robot control system may stop the robot's motion and enter an error state. Second level checks can compare individual force/torque components separately to ensure that they are within some predefined value range for a given robot operating mode. In some surgical situations or robot operating modes (e.g., pre-surgical positioning) the tolerance can be increased to cover unusual handling of the robot.

The comparison of the two detected force/torque values assumes that the RTA is not in contact with anything in the environment and that the operator is holding the instrument by the instrument handle. In addition, standard individual sensor sanity checks can be implemented to ensure that the sensor is functioning properly (e.g., signals are within expected value ranges). In practice, the SFT is much more robust to mechanical damage than the PFT, so the PFT is more likely to suffer critical mechanical failures before the SFT. This method can also be used for calibration or testing during operation when the robot is not being actively used. For example, an automated sensor testing routine can be used to compare the sensor readings in a variety of robot poses. A calibration instrument with a known mass can be used to further refine the diagnostics.

Handle Force/Torque Sensor Failure Detection through Frequency Analysis (FDFA)

An alternative to comparing the magnitude and direction of the two sensor readings is the detection and comparison of human hand tremor frequencies in the force/torque data. The cooperatively controlled robotic system inherently dampens undesired instrument motion by limiting accelerations and also by filtering out high frequency signals (using a low-pass filter with an 8 Hz cut-off) from the force/torque sensor input. The filtered force/torque signal is then used in admittance control. According to some embodiments, the cooperatively controlled robot detects sensor failure through frequency analysis by comparing frequency components of the signals from the $PFT_1$ and the $SFT_1$ resolved at the same position on the robot (in this case gravity compensation may not be necessary) before the low-pass filtering is applied. The frequency profile (e.g., using fast Fourier transform) for both should be very similar and a correlation metric, such as Normalized Cross Correlation (NCC), can be used to compare their similarity. If the similarity metric is below a certain threshold (s) in a given time interval (t), the force/torque sensing subsystem is in a compromised state and should be checked before continuing with normal operation. In some cases natural resonance of the system components may need to be considered and omitted from individual force/torque sensor readings before comparison.

Human Interaction Detection through Frequency Analysis (HIDFA)

The common embodiments of the cooperatively controlled robot platform use a foot pedal to adjust the admittance control gain. This has a convenient safety function in that the robot does not move unless the pedal is pressed. The operating room has many pedals and reducing the number of these is desirable.

An alternate method presented here verifies that the surgeon is indeed holding the surgical instrument attached to the robot, without using a pedal or a button. HIDFA enables and disables robot motion without a pedal. It involves analyzing the frequency spectrum of the force/torque input(s) for common hand-tremor frequency spectrum profiles (e.g., in the 2-20 Hz range) and only allowing robot motion when these signals are present for a given period of time (e.g., 1 second). The comparison can be computed with standard similarity metrics, e.g., NCC. The method assumes that the surgeon's interaction with the surgical instrument attached to the robot includes unique force/torque signatures that are only common to human instrument manipulation.

In an example scenario, the surgeon uses a modified surgical instrument where the unexpected weight causes a near constant bias force and as a result breaks gravity compensation. The cooperative control behaves properly until the surgeon releases the handle of the instrument and attends to something else. The bias force would cause undesirable robot motion due to gravity. This anomaly can be detected by the HIDFA since the frequency profile (mostly DC component) is significantly different than what is expected from common hand tremor. Accordingly, when the surgeon releases the tool, the robot can detect a change in the frequency profile, and can stop the motion of the tool. In addition, the same approach can be used to detect instrument collisions with inanimate objects that produce a unique vibration profile that is different from the typical human hand tremor profile. For example, assuming the robot has a hard shell, a collision with a hard object would initially generate a high frequency signal upon contact, followed by almost no vibration. The detection of the type of contact can be used to switch between different control strategies, e.g., whether to stop or continue motion.

To further improve detection sensitivity, multiple force/torque sensors are used to measure the forces/torques exerted on the robot. In addition, this same method is used to ensure that two sensors are working properly by actively comparing their ability to detect human interaction within some time and correlation tolerances.

The HIDFA is also used as a secondary safety reference for the following methods that allow the system to detect when the surgeon is holding the RTA, or the instrument handle, or both.

Arm Collision Detection

During standard force-guided robot motion (cooperative control), the force/torques resolved at $P_1$ as measured by the SFT and PFT should be equal (assuming gravity compensation for weight of the RTA at given robot pose) within some tolerance to account for sensor precision/noise or minor interactions with the environment. In the case when the RTA contacts a grounded object, where the contact point is between the two sensors, the SFT and PFT force/torque readings at $P_1$ will be different. This difference may indicate an undesirable collision of the arm with the anatomy. At this point the robot should stop and the surgeon should check the RTA for any contacts. If no contacts are apparent then there is a possibility that at least one of the force/torque sensors is not functioning properly. At this point the surgeon or technical assistant should run a calibration routine to ensure proper function of the force sensors.

Common alternative approaches for contact detection include contact sensing skins wrapping the robot's surface, on-board vision, strain gages, force load cells, and torque sensing at the joints. The DLR LWR robot (De Luca, 2006 [1]) serial robot arm uses only torque measurements at each robot joint to detect collisions by indirectly comparing the expected joint torques (based on a theoretical dynamic robot model) and the actual (measured) torque at the joints. However, not all possible collision situations are detected by this scheme. For example, with the robot at rest, true impulsive collision forces/torques cannot be detected. Furthermore, when the robot is in motion, collision can be only detected provided that the collision force influences the motion of the robot (i.e., the force/torque is in the rotation plane of at least one instrumented rotary joint). For this reason, the system presented here measures multiple degree-of-freedom forces/torques at multiple locations on the robot (not necessarily at the joints), to avoid such issues. Additionally, the joint torque approach to detecting collisions does not work in the case of a cooperatively-controlled robot, where the user holds the end-effector to guide the robot using force control. In this case, a robot using the joint torque approach would incorrectly interpret the user's contact as a collision.

With the addition of multiple secondary sensors, it is possible to estimate the contact point of the force on the robot arm by applying methods presented by He et al, 2014 [2]. The forces/torques measured by the SFTs are resolved at the collision contact point ($SFT_C$) and can be used to improve the robustness of collision detection by comparing the force/torque history and motion vectors prior to and during contact. Their profiles should be very similar. Of course this assumes that there is a single contact point and that its location is constant over the sampling time.

Additionally, the contact point location estimate can be communicated visually on a 3D model of the robot. It can also be incorporated into the motion control algorithm to prevent repeat collisions or to provide a warning to the surgeon when this location is approached again.

Cooperative Control of Main Robot Assembly

In some situations, the surgeon may want to only control the translation of the main robot assembly. According to some embodiments, this is achieved by enabling only the Delta stages, while the rest of the robot's joints (Roll/Tilt, others) remain inactive. This mode is enabled when the PFT sensor readings indicates no handle contact while the SFT readings indicates a contact with the RTA. In such case, it can be assumed that the operator is holding the RTA between the sensors. The SFT readings are then used as input into the cooperative control algorithm and the robot is actively guided to the desired XYZ position. To improve robustness of this control paradigm, the HIDFA can be used to verify the surgeon's interaction with the robot.

A practical embodiment includes an ergonomic handle that would encourage the operator to interact with the robot at a predefined location on the RTA (see FIG. 3). In this case the SFT is resolved at this secondary handle position for natural cooperative control interaction.

In a variation of this control mode, the translational and rotational motions can be controlled independently with two hands. For example, the FT input measured by SFT from the RTA handle input location (minus the FT measured by the PFT resolved at the RTA handle) can be used to translate the main robot assembly only, i.e., the Cartesian translation of the instrument. Simultaneously, the PFT input resolved at the instrument handle can be used to control the rotation of the instrument. In this way one hand is used to translate the tool while the other is used to rotate it. The division of which hand controls which degrees of freedom of the robot can be selected based on task requirements.

Two-Handed Gross Positioning Control

As described above and illustrated in FIG. 3, according to some embodiments of the invention, the cooperatively controlled robotic system includes an actuated gross positioning system (GPS). The GPS implementation can be an admittance or impedance controlled device and can have a combination of passive and active components. According to some embodiments, the GPS is mounted on the operating bed rail. According to some embodiments, the GPS is part of a cart that is connected to an operating table during surgery. The simplest version of the GPS provides a single degree of freedom motion that could be used to translate the system along the surgical bed.

The control of the GPS system can be enabled when the operator places one hand on the surgical instrument and the other hand on the RTA, and applies force/torque to both simultaneously. For convenience, the sensors' force/torque measurements can be resolved at the same point, e.g., $P_1$, including gravity compensation for the RTA. In the simplest case, the resultant force/torques are averaged ($FTM_1$) and the robot's GPS is controlled through a standard cooperative control algorithm where the desired robot velocity at the force resolution location is: $V_1 = J_1^{-1} * K * FTM_1$. The admittance gain K is preset to provide stable and intuitive control and the manipulator Jacobian $J_1$ for the GPS is calculated at location 1. This mode is engaged when both $SFT_1$ and $PFT_1$ (after gravity compensation of $SFT_1$ for weight of the arm and the instrument) are above some minimal magnitude, and the $SFT_1$ and $PFT_1$ are not equal within a predefined tolerance. This implies that there exists a force or torque applied on the RTA, besides the force or torque applied on the instrument handle. During the GPS control mode, the standard cooperative control of the instrument (i.e., the cooperatively controlled robot) can be disabled so that only the GPS is in motion.

To further improve the detection of the surgeon's intention to move the GPS, the directions of $SFT_1$ and $PFT_1$ can be considered. If the angle between the corresponding force/torque vectors is greater than the tolerance g, then the current GPS motion can be stopped and standard force control at the handle of the instrument can be engaged again.

Single-Handed Gross Positioning Control

According to some embodiments, the GPS force control is activated when an operator grabs the RTA. This event is detected by the embedded arm contact switch (ACS), which uses a standard method of contact sensing: pressure strip, capacitance, etc. For convenience this sensor is located on the RTA near the natural RTA handling area, possibly on the RTA handle itself. When the surgeon grabs the RTA and activates the contact sensor, the GPS control mode is enabled, while the cooperative robot (100 in FIG. 1) control is disabled. The SFT measurements are resolved at $P_A$ (gravity compensated for the weight of the robot components attached to the SFT sensor), and the robot GPS can be driven in the desired direction using a standard cooperative control algorithm. According to some embodiments, only the SFT is used as the input for force control of the GPS.

Alternatively, the GPS cooperative control can be enabled when no surgical instrument is in the instrument adapter and an SFT magnitude is above a preset threshold. This approach does not rely on a touch sensor.

During the GPS positioning mode the cooperative control of the instrument can function independently (controlled by manipulating the surgical instrument handle) or be completely disabled based on the surgeon's preference.

Instrument Pose Adjustment Control (IPAC)

In some surgical situations there exists a need to microadjust the robot pose while the instrument is not in the adapter. An example scenario is functional endoscopic sinus surgery where the robot is positioned near the nose. The Instrument Pose Adjustment Control is used to move the robot so that the adapter orientation and position is aligned with the sinus entry to facilitate partial manual instrument insertion in the anterior sinus so it can be quickly engaged with the instrument adapter. Since the instrument is not on the robot during the alignment phase, the surgeon does not have the physical interface (instrument handle) to control the position of the cooperatively controlled robotic system. Instead the surgeon can use the RTA handle to move the robot (a contact switch may be used for enabling IPAC mode). In IPAC control mode, the SFT is resolved at the typical location of the instrument handle, while the manipulator Jacobian JH is calculated at the instrument handle location and is used to calculate the desired velocity at the handle for admittance control: $V_H = J_H^{-1} * K * SFT_H$. (Note: $SFT_H$ is the Secondary Force/Torque sensor in the robot coordinate frame resolved at the instrument handle location assuming a virtual rigid body connecting the handle to the SFT). This allows the surgeon to translate and rotate the instrument adapter as if he or she were holding the instrument handle directly.

Instrument-Activated Gross Positioning Control

The robot system is outfitted with a method to recognize the type of instrument located in the instrument adapter. This is implemented in any of the standard methods, for example, RFID tag, electronic communication, computer vision, or direct user input (graphical user interface, voice control, etc.). A special non-surgical positioning instrument (PI) can be designated for adjusting the GPS. By inserting the instrument into the instrument adapter, the user can engage the GPS adjustment mode. The user applies a force on the instrument handle in the direction he or she would like to move the GPS and the system uses the readings from the force/torque sensor(s) to move the actuators to comply. The main advantage of using a specialized instrument for entering this mode is that it avoids unnecessary interaction with a graphical user interface. According to some embodiments, the instrument can contain or indicate a set of control parameters for the robot, such as ideal alignment parameters, workspace limits, compliance control gains, remote-center-of-motion constraint, instrument weight for gravity compensation, etc. The instrument shape can also provide a visual indication to the surgeon of the usable workspace for proper system alignment with the surgical site. Example PIs are shown in FIGS. 4A-4D and described in detail above.

Joystick Control

According to some embodiments, the Secondary Force/Torque sensor readings are converted into a velocity- or position-type joystick input that serves as a generic physical user-system interface. For example, instead of a mouse or a touch screen, the surgeon can press on the RTA to move the cursor on the screen.

This mode can be enabled when the readings on the PFT sensor are near zero (compensated for instrument weight) while the SFT readings are above a present threshold for a given period of time. This interaction method could be very beneficial in cases where the system requests a surgeon's input because it avoids the need for special User Interface buttons, and allows the surgeon to be near the patient while interacting with the system. Such input can be used to review 2D and 3D medical images, surgical plan, navigation data, change system settings, etc.

In practice, the RTA may benefit from an ergonomic handle. By assuming that the user is handling the arm by the handle, a more precise resolution of the input force/torque on the RTA is possible. More precise FT sensitivity enables a more natural mapping between the user's intention (force/torque) and the actual system response to the intention (mouse motion on the screen).

This idea is related to International Application No. PCT/US2015/051907, where a single primary FT sensor is used with the robot and serves as the input into a surgical system.

Mode Selection

It may be that not all of the interaction modes described herein are mutually compatible due to overlapping use of the force/torque sensors and contact sensors. In practice, the methods are chosen to cover the requirements of the surgical procedure and surgeon's preference. In addition, for added safety a foot pedal can be incorporated that controls the admittance gain value (K) and allows the robot or the GPS to move only when the pedal is engaged.

While the embodiments of the invention are described in the context of cooperatively controlled surgical robots, the concepts described herein can be applied to any system that uses an admittance control robot in a high-risk scenario where redundant user input force sensing may be required.

REFERENCES

[1] De Luca, Alessandro, and Raffaella Mattone. "Sensorless robot collision detection and hybrid force/motion control." Proceedings of the 2005 IEEE International Conference on Robotics and Automation. 2005.

[2] X. He et al. A Multi-Function Force Sensing Instrument for Variable Admittance Robot Control in Retinal Microsurgery. ICRA 2014.

[3] Balicki at al. Surgical System User Interface Using Cooperatively-Controlled Robot, Patent application (Patent application JHU#12957). 2014.

[4] Luca, A. Albu-Schaffer, S. Haddadin, and G. Hirzinger, "Collision Detection and Safe Reaction with the DLR-III Lightweight Manipulator Arm," 2006 IEEE/RSJ Int. Conf. Intell. Robot. Syst., pp. 1623-1630, October 2006.

[5] Intuitive Surgical—da Vinci System.

[6] U.S. Pat. No. 8,398,541—Interactive user interfaces for robotic minimally invasive surgical systems

[7] S. P. N. Singhy and C. N. Riviere, "Physiological tremor amplitude during retinal microsurgery," in Proceedings of the IEEE 28th Annual Northeast Bioengineering Conference, 2002, pp. 171-172.

[8] U.S. Pat. No. 5,417,210, J. Funda, D. LaRose, and R. Taylor, "Robotic System for Positioning a Surgical Instrument Relative to a Patient's Body", Filed Issue date May 27, 1992.

[9] U.S. Pat. No. 5,397,323, R. Taylor, J. Funda, D. Grossman, J. Karidis, and D. LaRose, "Remote center-of-motion robot for surgery", Filed Issue date Oct. 30, 1992.

[10] U.S. Pat. No. 5,397,323, R. H. Taylor, J. Funda, D. D. Grossman, J. P. Karidis, and D. A. LaRose, "Remote Center-of-Motion Robot for Surgery", Filed Mar. 14, Issue date

[11] U.S. Pat. No. 5,749,362, J. Funda, D. LaRose, and R. Taylor, "Method of creating an image of an anatomical feature where the feature is within a patient's body", Filed Issue date May 27, 1992.

[12] U.S. Pat. No. 5,887,121, J. Funda and R. H. Taylor, "Method of constrained Cartesian control of robotic mechanisms with active and passive joints", Filed Filed Jul. 17, 1997, Issue date Mar. 23, 1999.

[13] U.S. Pat. No. 6,201,984, J. Funda, D. LaRose, and R. Taylor, "System and method for augmentation of endoscopic surgery", Filed Issue date Jun. 13, 1991.

[14] U.S. Pat. No. 5,887,121, J. Funda and R. H. Taylor, "Method of constrained Cartesian control of robotic mechanisms with active and passive joints", Filed Filed Feb. 18, 1999, Issue date May 1, 2001.

[15] R. Taylor, J. Funda, D. LaRose, and M. Treat, "An Experimental System for Computer Assisted Endoscopic Surgery", in IEEE Satellite Symposium on Neuroscience and Technoloy, Lyons, 1992.

[16] J. Funda, R. Taylor, K. Gruben, and D. LaRose, "Optimal Motion Control for Teleoperated Surgical Robots", in 1993 SPIE Intl. Symp. on Optical Tools for Manuf. & adv. Autom., Boston, 1993.

[17] J. Funda, B. Eldridge, K. Gruben, S. Gomory, and R. Taylor, "Comparison of two mainpulator designs for laparoscopic surgery", in 1994 SPIE Int's Symposium on Optical Tools for Manufacturing and Advanced Automation, Boston, 1994.

[18] J. Funda, R. Taylor, B. Eldridge, K. Gruben, D. LaRose, and S. Gomory, "Image Guided Command and Control of a Surgical Robot", in Proc. Medicine Meets Virtual Reality II, San Diego, 1994. pp. 52-57.

[19] J. Funda, R. Taylor, S. Gomory, B. Eldridge, K. Gruben, and M. Talamini, Mark, "An experimental user interface for an interactive surgical robot", in 1st International Symposium on Medical Robotics and Computer Assisted Surgery, Pittsburgh, 1994.

[20] J. Funda, K. Gruben, B. Eldridge, S. Gomory, and R. Taylor, "Control and evaluation of a 7-axis surgical robot for laparoscopy", in Proc 1995 IEEE Int. Conf. on Robotics and Automation, Nagoya, Japan, May, 1995.

[21] R. H. Taylor, J. Funda, B. Eldgridge, S. Gomory, K. Gruben, D. LaRose, M. Talamini, L. Kavoussi, and J. anderson, "Telerobotic assistant for laparoscopic surgery.", IEEE Eng Med Biol, vol. 14-3, pp. 279-288, 1995.

[22] B. Eldridge, K. Gruben, D. LaRose, J. Funda, S. Gomory, J. Karidis, G. McVicker, R. Taylor, and J. Anderson, "A Remote Center of Motion Robotic Arm for Computer Assisted Surgery", Robotica, vol. 14-1 (Jan-Feb), pp. 103-109, 1996.

[23] U.S. Pat. No. 5,572,999, J. Funda, D. LaRose, and R. Taylor, "Robotic System for Positioning a Surgical Instrument Relative to a Patient's Body", Issue date May 27, 1992.

[24] J. Funda, R. Taylor, B. Eldridge, S. Gomory, and K. Gruben, "Constrained Cartesian motion control for teleoperated surgical robots", IEEE Transactions on Robotics and Automation, vol. 12-3, pp. 453-466, 1996.

[25] R. H. Taylor, J. Funda, B. Eldridge, K. Gruben, D. LaRose, S. Gomory, and M. D. Talamini, Mark, "A Telerobotic Assistant for Laparoscopic Surgery" in Computer-Integrated Surgery, R. Taylor, S. Lavallee, G. Burdea, and R. Moesges, Eds.: MIT Press, 1996, pp. 581-592.

[26] U.S. Pat. No. 7,035,716; Simon James Harris, Brian Lawrence Davies, Matjaz Jakopec, Active-constraint robots, Filing date: Jan. 29, 2002; Granted Apr. 25, 2006.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A cooperatively controlled robotic system, comprising:
a main robot assembly comprising mechanical links connected by actuated joints;
an arm assembly comprising a proximal end and a distal end, wherein said arm assembly is connected to said main robot assembly at said proximal end;
a tool assembly connected to said arm assembly at said distal end;
a first force sensor between said distal end of said arm assembly and said tool assembly,
a second force sensor between said proximal end of said arm assembly and said main robot assembly; and
a control system in communication with said main robot assembly, said arm assembly, said tool assembly, said first force sensor, and said second force sensor,
wherein said control system is configured to determine a force applied at said first force sensor based on a force detected by said second force sensor,
wherein said control system is further configured to compare said determined force to a force detected by said first force sensor, and
wherein said control system is further configured to detect a failure of at least one of said first and second force sensors based on said comparison.

2. The cooperatively controlled robotic system according to claim 1, wherein said first and second force sensors are six degree-of-freedom force sensors.

3. The cooperatively controlled robotic system according to claim 1, wherein said control system is further configured to detect a difference between said determined force and said force detected by said first force sensor, and stop motion of said main robot assembly, said arm assembly, and said tool assembly on a condition said difference exceeds a predetermined value.

4. The cooperatively controlled robotic system according to claim 1, wherein said control system is further configured to detect a collision between an object and said arm assembly based on said comparison.

5. The cooperatively controlled robotic system according to claim 1, wherein said control system is configured to stop motion of said arm assembly and allow motion of said main robot assembly on a condition that said second force sensor detects at least one force component and said first force sensor detects no force component.

6. The cooperatively controlled robotic system according to claim 1, wherein said control system is configured to move said arm assembly based on at least one force component applied to said tool assembly detected by said first force sensor, and to move said main robot assembly based on at least one force component applied to said arm assembly detected by said second force sensor.

7. The cooperatively controlled robotic system according to claim 1, further comprising a gross positioning system for positioning the cooperatively controlled robotic system in a surgical workspace.

8. The cooperatively controlled robotic system according to claim 7, wherein said control system is configured to activate said gross positioning system on a condition that said first force sensor detects at least one force component applied to said tool assembly that exceeds a first predetermined value and said second force sensor detects at least one force component applied to said arm assembly that exceeds a second pre-determined value.

9. The cooperatively controlled robotic system according to claim 7, wherein said control system is configured to activate said gross positioning system on a condition that a difference in direction between said force detected by said first force sensor and said force detected by said second force sensor does not exceed a pre-determined angle.

10. The cooperatively controlled robotic system according to claim 1, further comprising a contact switch on said arm assembly, wherein said contact switch is configured to detect contact by a user with said arm assembly.

11. The cooperatively controlled robotic system according to claim 7, further comprising a contact switch on said arm assembly, wherein said contact switch is configured to detect contact by a user with said arm assembly,
wherein said control system is configured to activate said gross positioning system on a condition that at least one force component applied to said tool assembly detected by said first force sensor indicates that no tool is in said tool assembly, and that said contact switch detects contact by said user with said arm assembly.

12. The cooperatively controlled robotic system according to claim 7, wherein said tool assembly comprises a tool recognition component, wherein said control system is configured to activate said gross positioning system on a condition that said tool recognition component indicates that a tool in said tool assembly is a non-surgical instrument.

13. The cooperatively controlled robotic system according to claim 1, wherein said control system is configured to control a user interface based on at least one force component applied by said user to said arm assembly detected by said second force sensor.

14. The cooperatively controlled robotic system according to claim 1, wherein said control system is configured to compare frequencies contained in said determined force and in the force detected by said first force sensor,
wherein said control system is further configured to detect a failure of at least one of said first and second force sensors based on said comparison of frequencies.

15. The cooperatively controlled robotic system according to claim 1, wherein said control system is further configured to detect a failure of at least one of said first and second force sensors based on predefined frequencies representing human interaction.

16. The cooperatively controlled robotic system according to claim 1, further comprising a third force sensor between said main robot assembly and a base of said robot;
wherein said control system is in communication with said third force sensor.

* * * * *